US007309501B2

(12) United States Patent
Walsh et al.

(10) Patent No.: US 7,309,501 B2
(45) Date of Patent: *Dec. 18, 2007

(54) CONDITIONED MEDIA TO INHIBIT GROWTH OF TUMOR CELLS

(75) Inventors: Catherine J. Walsh, Sarasota, FL (US); Carl A. Luer, Sarasota, FL (US)

(73) Assignee: Mote Marine Laboratory, Sarasota, FL (US)

( * ) Notice: Subject to any disclaimer, the term of this patent is extended or adjusted under 35 U.S.C. 154(b) by 105 days.

This patent is subject to a terminal disclaimer.

(21) Appl. No.: 11/132,797

(22) Filed: May 19, 2005

(65) Prior Publication Data

US 2005/0220893 A1 Oct. 6, 2005

Related U.S. Application Data

(63) Continuation-in-part of application No. 10/173,211, filed on Jun. 14, 2002, now Pat. No. 6,908,627.

(60) Provisional application No. 60/300,556, filed on Jun. 21, 2001.

(51) Int. Cl.
*A61K 35/60* (2006.01)
(52) U.S. Cl. .................. 424/520; 424/523; 424/577; 424/578
(58) Field of Classification Search ............... 424/520, 424/577, 578
See application file for complete search history.

(56) References Cited

U.S. PATENT DOCUMENTS

| | | |
|---|---|---|
| 5,075,112 A | 12/1991 | Lane |
| 5,192,756 A | 3/1993 | Zasloff et al. |
| 5,985,839 A | 11/1999 | Dupont et al. |
| 6,908,627 B2 * | 6/2005 | Walsh et al. ............... 424/559 |

OTHER PUBLICATIONS

Piferrer, FL and Callard, GV., Inhibition of Deoxyribonucleic Acid Synthesis During Premeiotic Stages of Spermatogenesis by a Factor from Tests—Associated Lymphomyeloid Tissue in the Dogfish Shark, Biology of Reproduction, 1995, pp. 390-398, vol. 53, Society for the Study of Reprollictron, Madison, WI, United States.

Walsh, CJ and Luer, CA, Comparative Pryocytic and pryocytic activities of Leucocytes from Peripineral Blood and Lymphomycloid tissues of the Nurse Shark and Clearnose Skate, Fish and Shellfish Immunology, 1998, pp. 197-215, vol. 8, Academic Press, United States.

Luer, CA, Walsh, CJ, Bodine, AB, Wyffels, JT., Scott, TR., The Elasmodrancin Thymus: Anatomical, thstological, and Preliminary Functional Characterization, The Journal of Experimental toology, 1995, pp. 342-354, 101. 273, Wiley-Liss, United States.

McKinney, EL, Shark Lymphocytes: Primitive Antigen Reactive Cells, Annual Review of Fish Diseases, 1992, pp. 43-51, vol. 2, Pergamon Press, United States.

Fänge, R. and Mattison, A. The Lyphomyeloid (Hematopoietic) System of the Atlantic Nurse Shark, Giviglyinostoma cirratum, Biol Bull,, 1981, pp. 240-249, vol. 160, The Marine Biological Laboratory, United Staes.

Lloyd-Evans, P., Development of the Lymphomyeloid System in the Dogfish, Scyliorhinus Canicula, Developmental and Comparative Immunology, 1993, pp. 501-514, vol. 17, Pergamon Press, United States.

Fange, R, and Pulsford,A. Structural Studies on Lymphomyeloid Tissues of the Dogfish, Scyliorhinus L., Cell and Tissue Research, 1983, pp. 337-351, vol. 230, Springer-Verlag, Germany.

Lee, A. and Langer, R, Shark Cartilage Contains Inhibitors of Tumor Angrogenesis, Science, 1983, pp. 1185-1189, vol. 221, American Association for the Advancement of Science, United States.

Folkman, J. and Klagsbrun, M., Angiogenic Factors, Science, 1987, pp. 442-447, vol. 235, American Association for the Advancement of Science, United States.

Walsh CJ, AB Bodine, DR Noyes, CA Luer. Preliminary evaluation of tumor cell growth inhibition by conditioned media from in vitro cultures of nurse shark (Ginglymostoma cirratum and clearnose skate (Raja eglanteria) immune cells. American Elasmobranch Society, 16th Annual Meeting, La Paz, Mexico, Jun. 14-20, 2000, p. 367, USA.

Noyes DR, CJ Walsh, CA Luer. Growth inhibition of mammalian tumor cell lines by conditioned media from in vitro cultures of immune cells from the epigonal organs of bonnethead sharks, Sphyma tiburo. American Elasmobranch Society, 17th Annual Meeting, State College, PA, Jul. 5-10, 2001, p. 104, USA.

Walsh CJ, CA Luer, GA Hunter, DR Noyes, CA Smith, M Gasparetto, KN Bhalla, R Nimmanapalli. Bioactive compounds from bonnethead shark Sphyrna tiburo epigonal cells: inhibitory activity against tumor cell lines. American Elasmobranch Society, 18th Annual Meeting, Jul. 3-8, 2002, pp. 300-301, USA.

Walsh CJ, CA Luer, DR Noyes, CA Smith, M Gasparetto, KN Bhalla. Characterization of shark immune cell factor (Sphyrna tiburo epigonal factor, STEF) that inhibits tumor growth by inhibiting S-phase and inducing apoptosis via the TRAIL pathway. FASEB J, vol. 18, No. 4, Mar. 23, 2004, pp. A60-A61, Washington DC ,USA.

Walsh CJ, CA Luer, DR Noyes, CA Smith, M Gasparetto, KN Bhalla. Characterization of shark immune cell factor (Sphyrna tiburo epigonal factor, STEF) that inhibits tumor growth by inhibiting S-phase and inducing apoptosis via the TRAIL pathway. Experimental Biology 2004, Apr. 17-21, 2004, Washington DC, USA.

* cited by examiner

*Primary Examiner*—Leon B Lankford, Jr.
*Assistant Examiner*—Taeyoon Kim
(74) *Attorney, Agent, or Firm*—Catherine J. Walsh; Cecilia A. Walsh

(57) ABSTRACT

Conditioned media compositions having valuable biological activity are obtained from cultures of immune cells from elasmobranch fishes. A method is provided for producing the conditioned media compositions. Conditioned media obtained using epigonal cells from bonnethead sharks (*Sphyrna tiburo*) and lemon sharks (*Negaprion brevirostris*) demonstrate strong anti-tumor activities. The conditioned media compositions can be used for treating tumor proliferation.

20 Claims, 15 Drawing Sheets

SDS-PAGE of bonnethead epigonal CM
Lane 1: standard molecular weight proteins
Lane 2: spleen CM proteins
Lane 3: PBL CM proteins
Lane 4: epigonal CM proteins

**Effect of enzyme treatment on bioactivity of *S. tiburo* epigonal CM**

Figure 11.

CONDITIONED MEDIA TO INHIBIT GROWTH OF TUMOR CELLS

CROSS REFERENCE TO RELATED APPLICATION

This application is a continuation-in-part of U.S. patent application Ser. No. 10/173,211, filed Jun. 14, 2002 now U.S. Pat. No. 6,908,627 which claims priority from Provisional Application Ser. No. 60/300,556, filed Jun. 21, 2001, entitled "Conditioned Media to Inhibit Growth of Tumor Cells," the disclosures of which are incorporated herein by reference.

FIELD OF THE INVENTION

This invention relates to conditioned media compositions made from immune cells from elasmobranch fishes, to methods of making such compositions, to anti-tumor compounds comprising such compositions, and to anti-tumor treatment methods comprising such compositions.

BACKGROUND OF THE INVENTION

Elasmobranch fishes (sharks, skates, and rays) are relatively disease-free (Wellings, 1969), particularly with regard to the lack of cancerous tumors. As documented by the Registry of Tumors in Lower Animals maintained at the Smithsonian Institution (Harshbarger, 1965-present), a few tumors have been described from this large subclass of fish, but their incidence is acknowledged to be a rarity. Since elasmobranchs are notably resistant to tumor development, these fish have been well studied with regard to their cancer resistance. The immune system in elasmobranchs has been studied to investigate anti-tumor and cytokine-like factors present in their immune systems. Compared to other lower vertebrate animal systems, relatively little functional information is available regarding the cells and tissues which comprise the elasmobranch immune system (McKinney, 1992). While elasmobranchs do not have bone marrow, they do have a thymus (Fänge and Pulsford, 1983; Lloyd-Evans, 1993; Luer et al., 1995) and a spleen, as well as two lymphomyeloid organs which are unique to this subclass of fish, the Leydig organ surrounding the esophagus, and the epigonal organ associated with the gonads. Histologically, the Leydig and epigonal organs of elasmobranchs resemble bone marrow and lymph nodes of higher vertebrates and are very active in granulopoiesis and lymphocyte production (Fänge and Mattisson, 1982; Fänge, 1987, 1994). While many elasmobranchs possess both of these lymphoid organs, some have only the epigonal organ (Honma et al., 1984; Fänge, 1987). Other than the role of these tissues in granulopoiesis and lymphopoiesis, little is known of the functional aspects of the cells within these unique tissues. Cells produced by the epigonal and/or Leydig organs may be important in immune responses and in inflammatory processes of elasmobranchs (Fänge and Mattisson, 1981).

Shark cartilage has been studied with regard to its antiangiogenic properties. Lee and Langer (1983) and Folkman and Klagsbrun (1987) have shown that sharks produce a substance which inhibits neovascularization. There are several therapeutically valuable compounds isolated from sharks. For example, U.S. Pat. No. 5,192,756 discloses a compound having antibiotic and antiprotozoal properties isolated from the stomach of a dogfish shark. U.S. Pat. No. 5,075,112 describes a method for inhibiting angiogenesis using shark cartilage, and U.S. Pat. No. 5,985,839 describes extracts of shark cartilage having anti-angiogenesis properties and an inhibitory effect on cell tumor lines.

An antimitogenic factor derived from the epigonal organ of a dogfish shark was shown to reversibly inhibit DNA synthesis in spermatocysts in the testis (Piferrer and Callard, 1995). Previously, juvenile (total length<75 cm) nurse shark (*Ginglymostoma cirratum*) epigonal cells and clearnose skate (*Raja eglanteria*) epigonal and Leydig organ cells were placed into short-term culture (Walsh and Luer, 1998). These cultures included a cell culture medium that had been modified to approximate the normal osmolarity (970 mOsm) of elasmobranch cells using urea, NaCl, and trimethylamine N-oxide (TMAO) to balance the medium isotonically. Urea is a major balancing osmolyte naturally present in marine cartilaginous fish, including elasmobranch fishes. TMAO is a solute naturally concentrated in the urea-rich cells of elasmobranchs that serves to offset the damaging effects of urea on intracellular protein structure and function by raising the free energy of the denatured state of proteins, and also stabilizes the osmolyte urea. These preparations were not evaluated for anti-tumor activity. Therapeutically valuable biological activity demonstrated by a factor isolated from cultures of immune cells of elasmobranchs has not yet been described.

SUMMARY OF THE INVENTION

The present invention provides compositions having therapeutically valuable biological activities obtained from cultures of immune cells from elasmobranch fishes (especially sharks from Order Carcharhiniformes), to methods for producing these compositions, to anti-tumor compounds compounds comprising these compositions, and to anti-tumor treatment methods comprising these compositions. The compositions are prepared from cell culture supernatants and are referred to as conditioned media (CM). Among the therapeutically valuable activities obtained, irreversible anti-tumor proliferating activities have been confirmed to be present in useful concentrations which consistently demonstrate more than 80% growth inhibition against tumor cell lines in a dose-dependent fashion. Compositions having therapeutically valuable biological activities can be obtained from dialyzed and lyophilized conditioned media compositions.

In a first aspect, this invention provides a method for preparing a conditioned media composition having non-reversible anti-tumor activity comprising the steps of:
(1) providing pieces of tissue comprising immune cells from an elasmobranch fish,
(2) culturing and incubating the pieces of tissue in a cell culture medium under serum-free conditions, and
(3) removing cells from the cell culture medium comprising the cultured and incubated pieces of tissue to produce a cell-free supernatant comprising molecules produced by the immune cells,
wherein the cell culture medium has osmolarity of 800-1200 mOsm and comprises urea and a salt and does not comprise trimethylamine N-oxide.

In a second aspect, this invention provides a conditioned media composition having non-reversible anti-tumor activity, wherein the conditioned media composition is prepared by a method comprising the steps of:
(1) providing pieces of tissue comprising immune cells from an elasmobranch fish,
(2) providing a cell culture medium having osmolarity of 800-1200 mOsm and comprising urea and a salt and not comprising trimethylamine N-oxide, (3) culturing and incubating the pieces of tissue in the cell culture medium under serum-free conditions, and (4) removing cells from the cell culture medium containing the cultured and incubated pieces of tissue to produce a cell-free supernatant comprising molecules produced by the immune cells.

In a third aspect, this invention provides a method for preparing a conditioned media composition having anti-tumor activity comprising the steps of:

(1) providing pieces of tissue comprising immune cells from a shark of Order Carcharhiniformes, (2) culturing and incubating the pieces of tissue in a cell culture medium under serum-free conditions, and (3) removing cells from the cell culture medium comprising the cultured and incubated pieces of tissue to produce a cell-free supernatant comprising molecules produced by the immune cells, wherein the cell culture medium has osmolarity of 800-1200 mOsm and comprises urea and a salt.

In a fourth aspect, this invention provides a conditioned media composition having anti-tumor activity, wherein the conditioned media composition is prepared by a method comprising the steps of:

(1) providing pieces of tissue comprising immune cells from a shark of Order Carcharhiniformes, (2) providing a cell culture medium having osmolarity of 800-1200 mOsm and comprising urea and a salt, (3) culturing and incubating the pieces of tissue in the cell culture medium under serum-free conditions, and (4) removing cells from the cell culture medium containing the cultured and incubated pieces of tissue to produce a cell-free supernatant comprising molecules produced by the immune cells.

In a fifth aspect, this invention provides a conditioned media composition having substantially non-reversible anti-tumor activity, wherein the conditioned media composition is prepared by steps comprising:

(1) providing tissue from an elasmobranch fish, (2) providing a cell culture medium having osmolarity of 800-1200 mOsm and comprising urea and a salt, (3) culturing and incubating the tissue in the cell culture medium under serum-free conditions, and (4) removing cells from the cell culture medium to produce a cell-free supernatant, wherein tumor cell growth does not substantially resume after removal of the conditioned medium. The tumor cell growth further does not resume after washing of the tumor cells and resuspension or reculture of the tumor cells in a fresh cell culture medium not containing the conditioned medium (e.g., shark epigonal conditioned medium). The antitumor activity of the conditioned medium preferentially targets tumor cells compared with normal cells. In a preferred embodiment, the antitumor activity of the conditioned medium is increased by partial purification of conditioned medium using trypsin digestion of proteins therein and separation and retention of tryptic peptide fragments. The tryptic peptide fragments are then used in the conditioned medium.

BRIEF DESCRIPTION OF THE DRAWINGS

The present invention will be readily understood by way of the specific embodiments shown in the appended figures, the purpose of which is to illustrate the invention rather than to limit its scope.

FIG. 11 shows treatment of bonnethead shark epigonal conditioned medium with protease reduces growth inhibitory activity against tumor cell lines.

DETAILED DESCRIPTION OF THE INVENTION

Figure 1:
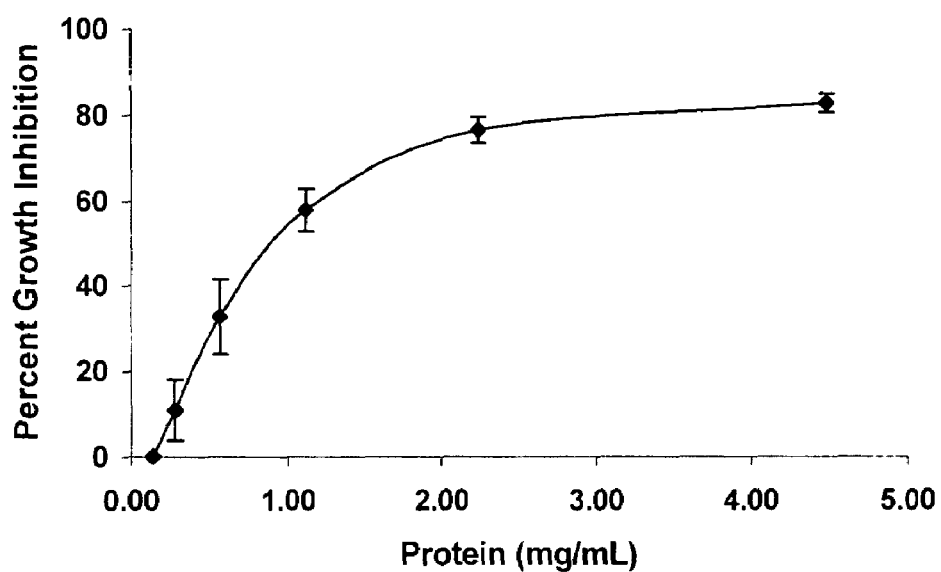
FIG. 1 shows a dose-response growth inhibitory activity of bonnethead shark epigonal conditioned media prepared according to the invention on A375.S2 cell line.

The foregoing detailed description of the invention includes passages which are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions thereof relate to specific embodiments of the invention, it is to be understood that where a specific feature is disclosed in the context of a particular figure, such feature can also be used, to the extent appropriate, in the context of another figure, in combination with another feature, or in the invention in general.

The immune cells used in the present invention come from elasmobranch fishes, including sharks, rays and skates. It is preferred that the immune cells come from tissue from the Leydig or epigonal organ of elasmobranch fishes. It is especially preferred that the immune cells come from tissue from the epigonal or Leydig organ of a shark from Order Carcharhiniformes or from Order Orectolobiformes. It is particularly preferred that the immune cells come from tissue from the epigonal or Leydig organ of a shark in the family Carcharhinidae (e.g., lemon, bull, blacknose, blacktip, tiger, and sandbar sharks) or in the family Sphyrnidae (e.g., bonnethead, hammerhead, and scalloped hammerhead) or in the family Ginglymostomatidae (e.g., nurse shark). If a shark in the family Ginglymostomatidae is used, it is preferred that the shark have overall length longer than 75 cm. It is most especially preferred that the immune cells come from tissue from the epigonal organ of a bonnethead shark (*Sphyrna tiburo*) or lemon shark (*Negaprion brevirostris*). The elasmobranch fishes which supply the immune cells for this invention may be either male or female.

It is preferred that the elasmobranch used as the source of immune cells be healthy and that the tissue be collected under aseptic conditions. For making the CM described herein, it is preferred that the tissue be used fresh, immediately following excision from the animal, or as soon as possible following excision from the animal, preferably not to exceed 24 h. It is preferred that tissue from neighboring organs be carefully removed by dissection. For example, if an epigonal organ is to be used as the source of immune cells, then it is preferred that any gonadal tissue be excised and discarded. In addition, it is preferred that the tissue be rinsed with sterile elasmobranch-modified phosphate buffered saline solution (E-PBS) to remove any external blood or other body fluids. For example, the E-PBS used can comprise NaCl and $NaH_2PO_4$ which has been pH adjusted to 7.2-7.4 and has been filter sterilized. Small pieces of the tissue being used as the source of the immune cells should be provided, e.g., the tissue can be minced into pieces smaller than 5 $mm^2$ under sterile conditions. Unless it is processed immediately, the tissue should be kept cold (e.g., 4° C.) after dissection and before mincing.

The present invention describes a conditioned media composition made from elasmobranch immune cells having therapeutically valuable biologically active components (e.g., irreversible anti-tumor activity) using a cell culture medium which has been modified to approximate the normal osmolarity of elasmobranch cells, and a method of preparation thereof. For some embodiments, it is preferred that the conditioned media composition does not contain TMAO. It is preferred that the osmolarity of the cell culture medium be 800-1200 mOsm, particularly 900-1100 mOsm, especially 950-1000 mOsm, most especially 970 mOsm. The osmolarity of the cell culture medium can be adjusted using urea and salt. It is preferred that the salt used be sodium chloride. In addition, antibiotics (e.g., penicillin, streptomycin sulfate, neomycin, and Amphotericin B) and DNAse (deoxyribonuclease) can be added to the modified cell culture medium. Conditioned media compositions from shark epigonal organs as described herein demonstrate consistent anti-tumor activity at high levels (e.g., greater than 70%, or greater than 80%). Finally the pH of the modified cell culture medium can be adjusted to near neutral pH, e.g., 7.0-7.4. It is preferred that the modified cell culture medium be filter sterilized before use.

The present invention also describes a conditioned media composition made from immune cells from tissue from the epigonal or Leydig organ of a shark from Order Carcharhiniformes having therapeutically valuable biologically active components (e.g., irreversible anti-tumor activity) using a cell culture medium which has been modified to approximate the normal osmolarity of elasmobranch cells, and a method of preparation thereof. It is especially preferred that the sharks be in the family Carcharhinidae (e.g., lemon, bull, blacknose, blacktip, tiger, or sandbar sharks) or in the family Sphyrnidae (e.g., bonnethead, hammerhead, or scalloped hammerhead sharks). It is most especially preferred that the immune cells come from tissue from the epigonal organ of a bonnethead shark (*Sphyrna tiburo*) or lemon shark (*Negaprion brevirostris*). It is preferred that the osmolarity of the cell culture medium be 800-1200 mOsm, particularly 900-1100 mOsm. especially 950-1000 mOsm, most especially 970 mOsm. The osmolarity of the cell culture medium can be adjusted using urea and salt (e.g., NaCl). In addition, antibiotics (e.g., penicillin, streptomycin sulfate, neomycin, and Amphotericin B) and DNAse can be added to the modified cell culture medium. The pH of the modified cell culture medium can be adjusted to near neutral pH, e.g., 7.0-7.4. It is preferred that the modified cell culture medium be filter sterilized before use.

The small pieces of tissue comprising immune cells from the elasmobranch fishes are incubated in the modified cell culture medium under serum-free conditions for two to four days. It is preferred that the incubation be carried out between 20-29° C., under 4-10% $CO_2$ for 1-7 days. It is especially preferred that the incubation be carried out at 25° C., under 5% $CO_2$ for 2-4 days. After incubation, a cell-free conditioned media can be prepared, preferably by centrifugation, although any suitable technique may be used (e.g., filtration). The cell-free conditioned media can be further processed by dialysis against a buffer solution or water, lyophilization, and reconstitution in a mammalian tissue culture medium or other buffer. Alternatively, if it is not desired to process the conditioned media directly after its preparation, the conditioned media can be prepared through step 3) of the first and third aspect of the invention or step 4) of the second and fourth aspects of the invention, and subsequently stored under cold conditions, preferably below 0° C. (e.g., −20° C. or −80° C.), for as long as desired, and then restored to room temperature and dialyzed against a buffer solution or water and lyophilized and reconstituted in mammalian tissue culture media or other buffer. The lyophilized samples can be stored frozen, (e.g., −20° C. to −80° C.), preferably −80° C. until use in assays. Preferably dialysis is carried out with dialysis tubing having 6000-8000 Da molecular weight cut off (hereinafter, MWCO), but MWCO ranging from 1000 Da-100 kDa may also be used.

The cells removed from the conditioned media can be placed into culture for a second harvest while maintaining sterile conditions. Fresh cell culture media (modified according to the method described herein) should preferably be used to re-culture the cells. The cells should be re-incubated according to the method described herein. Such resuspension of elasmobranch immune cells in fresh cell culture medium results in conditioned medium with antitumor activity substantially equivalent to initial harvest.

The cell-free conditioned media compositions described herein have been tested for anti-tumor activity on tumor cell lines A375.S2 [human malignant melanoma, American Type Culture Collection (ATCC) number CRL-1872], WEHI 164 (mouse fibrosarcoma, ATCC number CRL-1751), Daudi (human Burkitt's lymphoma, ATCC number CCL 213), MCF-7 (human breast carcinoma; ATCC number HTB-22), HCC38 (human breast ductal carcinoma; ATCC number CRL-2314), and MDA-MB-435S (human breast ductal carcinoma; ATCC number HTB-129).

Figure 2:
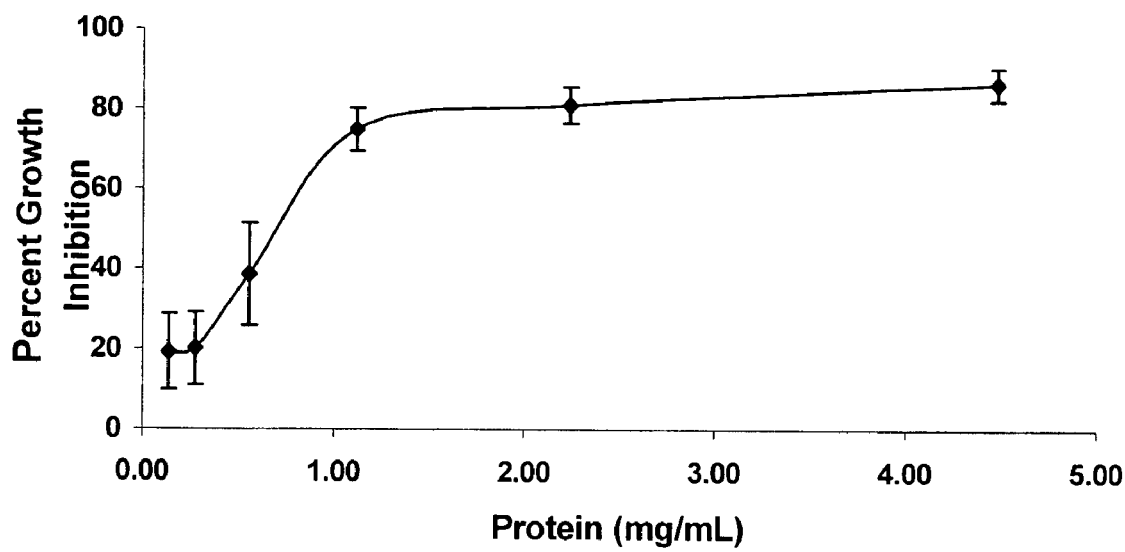
FIG. 2 shows a dose-response growth inhibitory activity of bonnethead shark epigonal conditioned media prepared according to the invention on WEHI 164 cell line.
Figure 3:
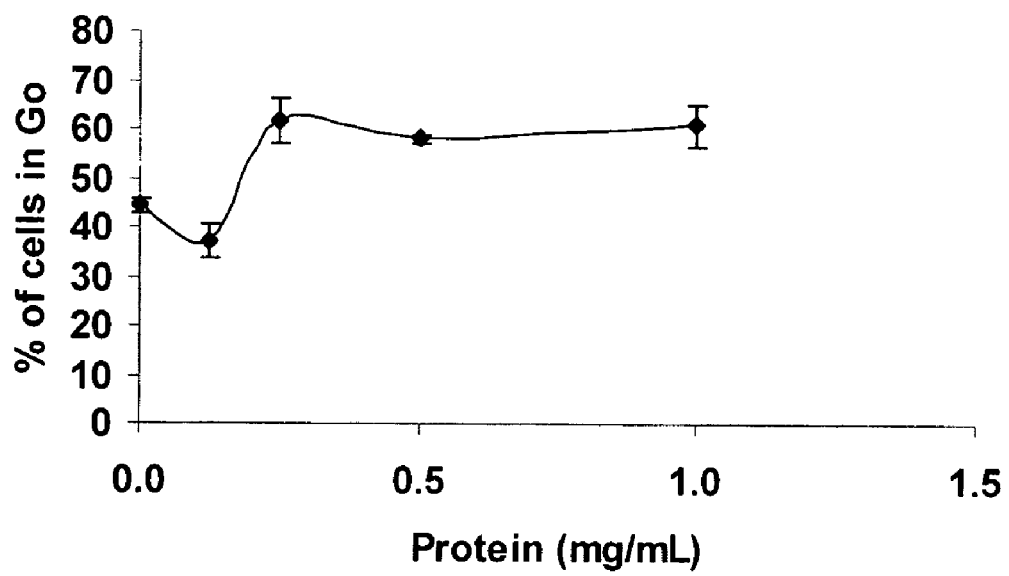
FIG. 3 shows the effect of bonnethead epigonal conditioned media preparations according to the invention on the Go phase of the cell cycle in Daudi cell line.
Figure 4:
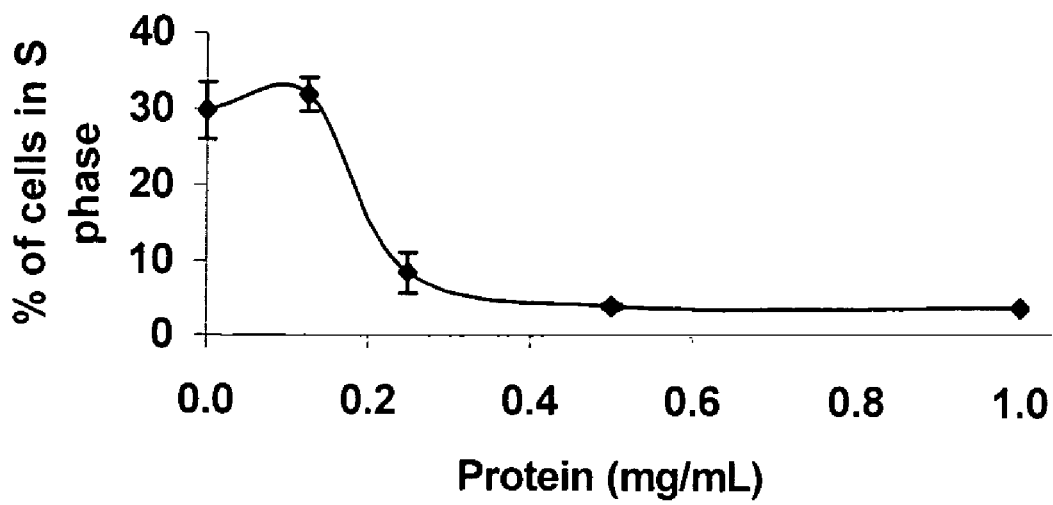
FIG. 4 shows the effect of bonnethead epigonal conditioned media preparations according to the invention on the S phase of the cell cycle in Daudi cell line.
Figure 5:
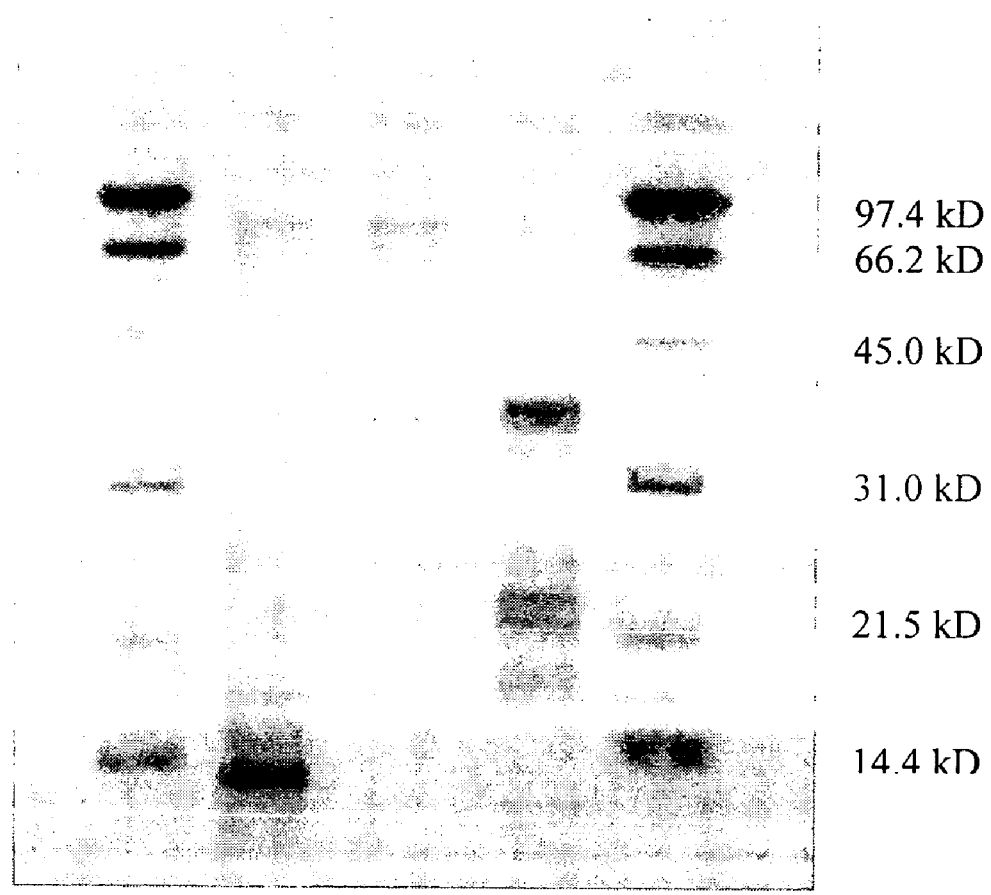
FIG. 5 shows the electrophoretic profile on SDS-PAGE of bonnethead epigonal conditioned media according to the invention. Lane 1: Standard molecular weight proteins; Lane 2: Spleen CM proteins which show no tumor inhibitory activity: Lane 3: Peripheral blood leukocytes (PBL) CM proteins which show no tumor inhibitory activity: Lane 4: Epigonal CM proteins from cultured media preparations according to the invention; Lane 5: Standard molecular weight proteins.
Figure 6:
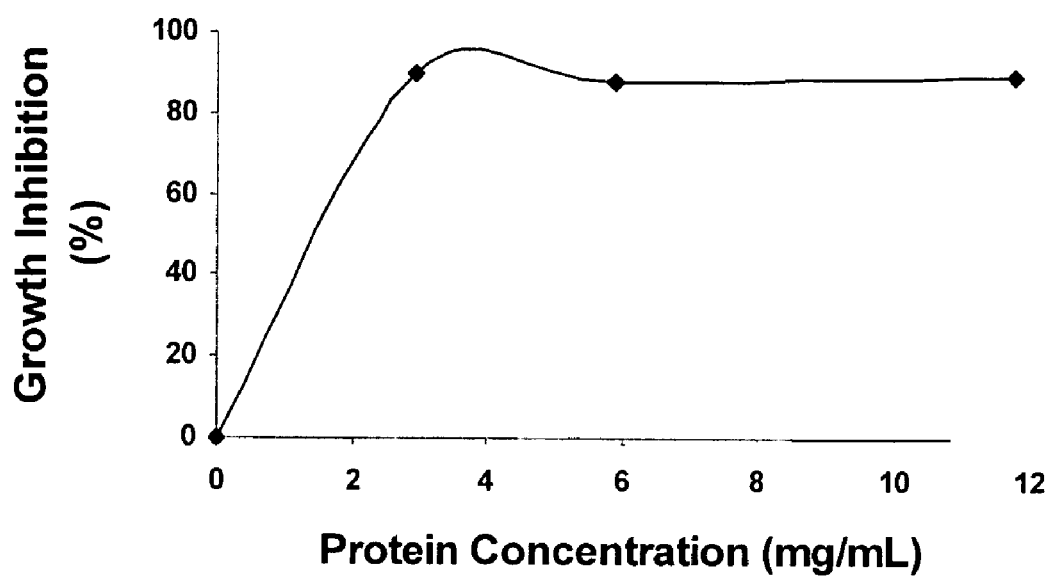
FIG. 6 shows dose-response growth inhibitory activity of lemon shark epigonal CM preparations according to the invention on A375.S2 cell line.
Figure 7:
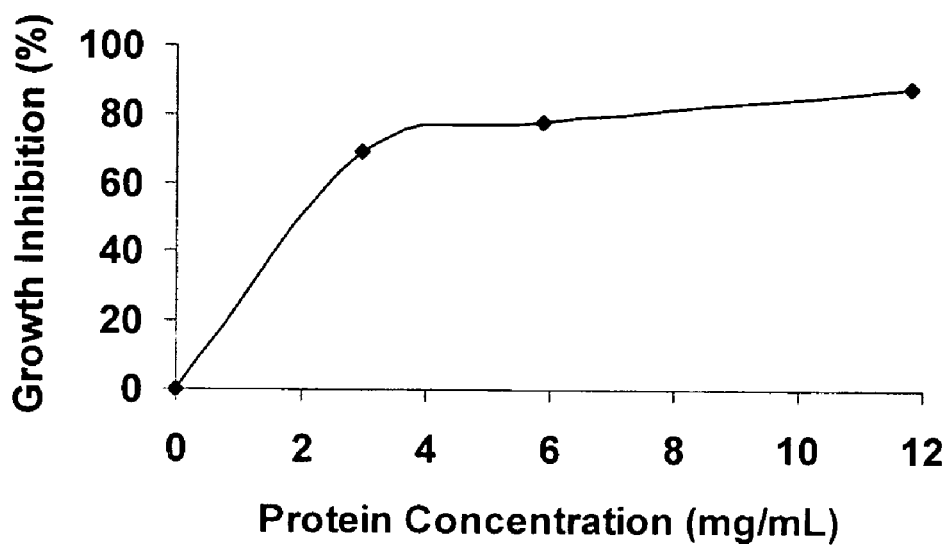
FIG. 7 shows dose-response inhibitory activity of lemon shark epigonal CM preparations on WEHI 164 cell line.

The invention is illustrated by the following drawings in which FIGS. 1 and 2 show that conditioned media prepared using tissue from an epigonal organ of a bonnethead shark using the method described herein is effective in inhibiting growth of more than 80% of the A375.S2 cells and WEHI 164 cells in culture, respectively. FIG. 3 shows that the percentage of Daudi cells remaining in the Go phase of the cell cycle are increased by approximately 35% (33-37%) when treated with conditioned media prepared using tissue from an epigonal organ of a bonnethead shark using the method described herein. FIG. 4 shows that the percentage of Daudi cells entering the S phase of the cell cycle, when treated with epigonal conditioned media, is 85% less than the percentage of untreated Daudi cells entering the S phase of the cell cycle. Conditioned media prepared using tissue from epigonal organs of bonnethead shark inhibit cell division in tumor cells. Conditioned media compositions prepared from the spleen or peripheral blood leukocytes from the same animal demonstrate no tumor inhibitory activity (FIG. 5). FIGS. 6 and 7 show that conditioned media prepared using tissue from an epigonal organ of a lemon shark using the method described herein is effective in inhibiting growth of more than 85% of A375.S2 cells and more than 80% effective in inhibiting growth of WEHI 164 cells. All anti-tumor activity demonstrated by the conditioned media compositions described herein is substantially non-reversible, i.e., if the anti-tumor composition described herein is removed from the cell tumor lines and the lines are washed, tumor cell growth does not resume.

Figure 8:
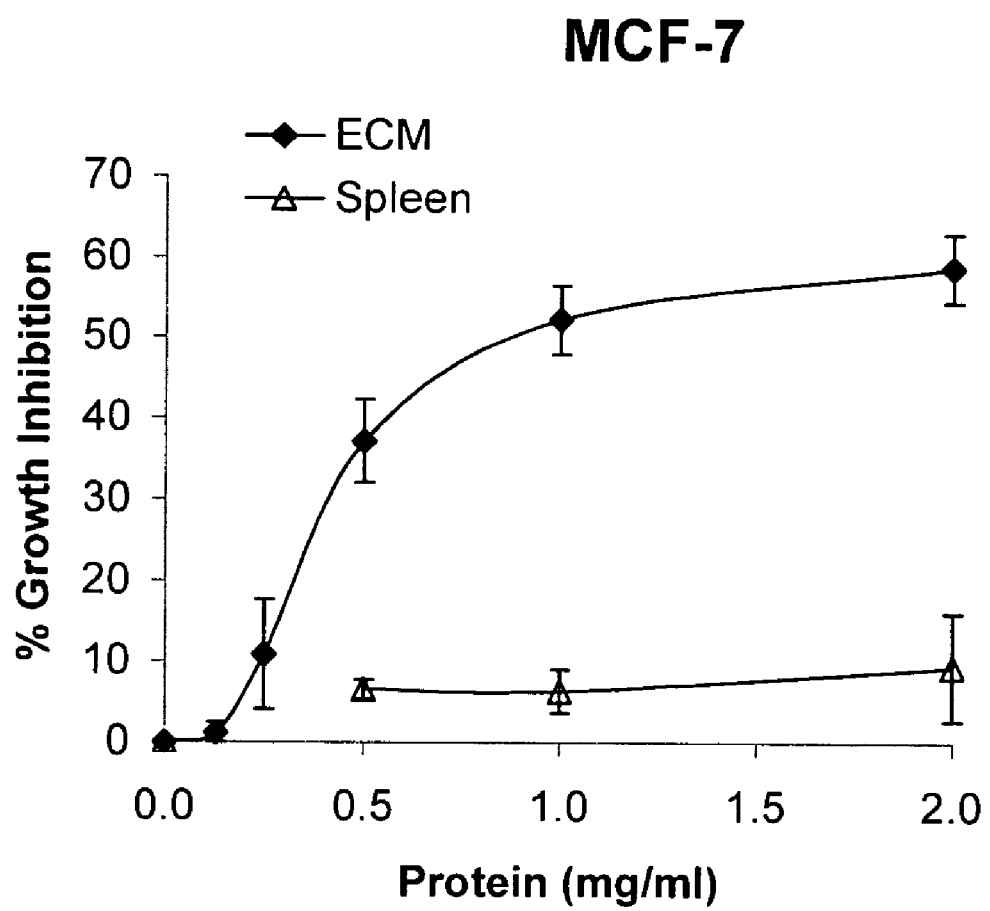
FIG. 8 shows dose-response inhibitory activity of bonnethead shark epigonal conditioned medium and spleen conditioned medium preparations against a cell line derived from breast cancer cells, MCF-7.

FIG. 8 shows growth inhibitory activity of bonnethead shark epigonal and spleen conditioned media preparations against a cell line derived from breast cancer cells, MCF-7. FIG. 8 shows that conditioned medium prepared using tissue from an epigonal organ of a bonnethead shark using the method described herein is effective in inhibiting growth of more than 60% of MCF-7 cells but conditioned medium compositions prepared from the spleen from the same animal demonstrate no tumor inhibitory activity.

Figure 9:
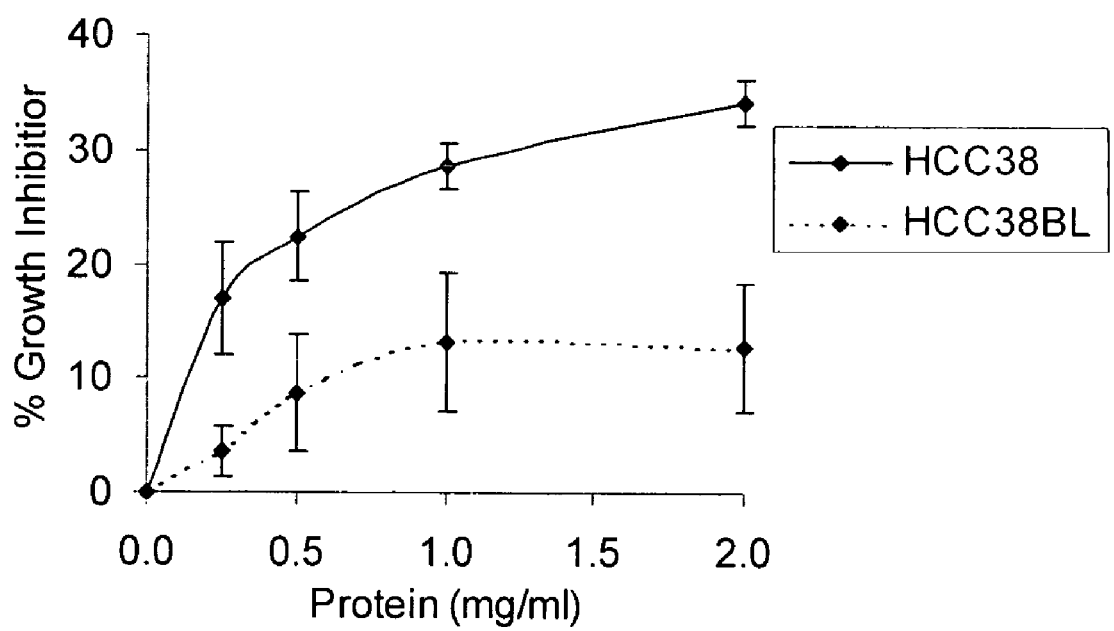
FIG. 9 shows preferential growth inhibitory activity of bonnethead shark epigonal conditioned medium towards malignant tumor cells (HCC38) compared with non-malignant, non-tumor normal cells (HCC38BL).

The cell-free conditioned media composition described herein has been tested for anti-tumor activity on a non-tumor cell line, HCC38BL (B lymphoblastoid cell line; ATCC number CRL-2346). FIG. 9 shows preferential growth inhibitory activity of bonnethead shark epigonal conditioned media compositions towards malignant tumor cells (HCC38) as compared with non-malignant, non-tumor normal cells (HCC38BL). FIG. 9 shows that conditioned media prepared using tissue from an epigonal organ of a bonnethead shark using the method described herein is effective in inhibiting growth of approximately 40% of malignant HCC38 cells but less than 12% of non-malignant HCC38BL cells.

Figure 10:
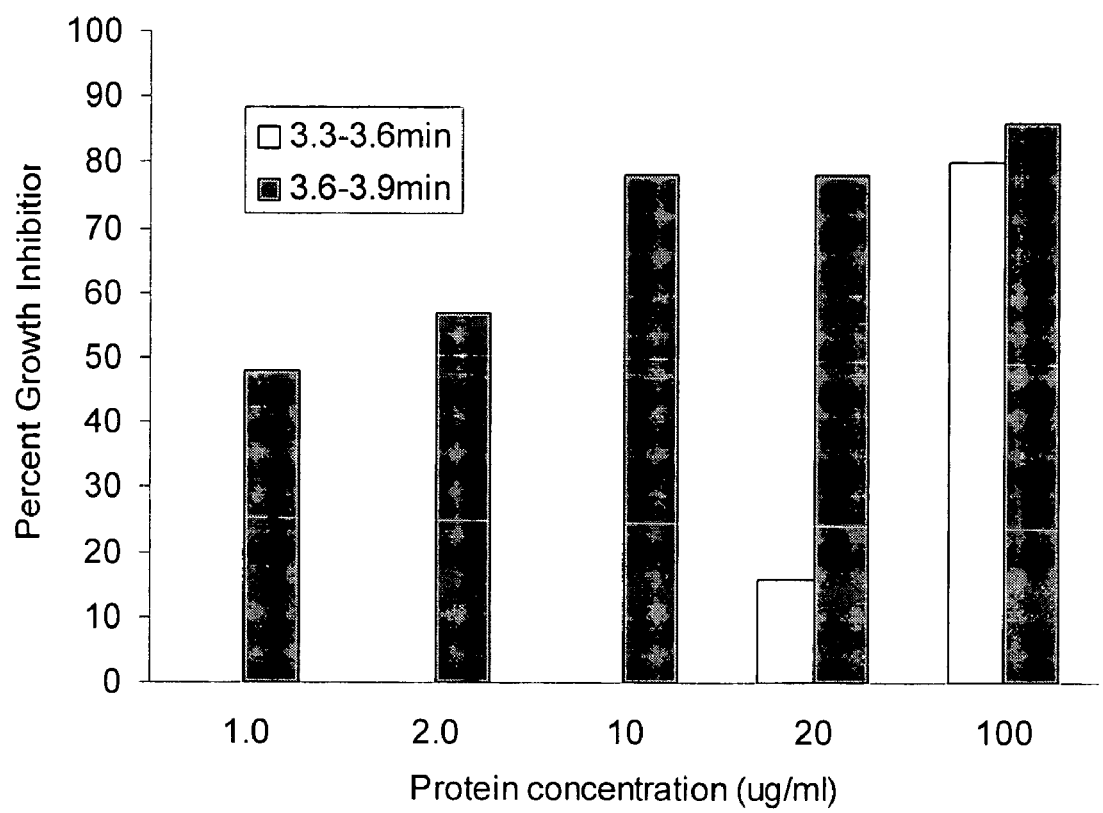
FIG. 10 shows substantial increase in growth inhibitory activity of bonnethead shark epigonal conditioned medium at considerably lower protein concentration resulting from partial purification using tryptic digests.

FIG. 10 shows substantial increase in growth inhibitory activity of bonnethead shark epigonal conditioned medium at considerably lower protein concentration resulting from partial purification using tryptic digests. Tryptic digest fractions with retention times of 3.6-3.9 min using high-pressure liquid chromatography resulted in almost 50% growth inhibitory activity against MDA-MB-435S breast carcinoma cells at a protein concentration of 1 ug/ml. This growth inhibitory activity represents an approximately 1000-fold increase in growth inhibitory activity per microgram of protein compared with bonnethead shark epigonal conditioned medium compositions that have not been treated with trypsin digestion and peptide fragments separated using high pressure liquid chromatography.

FIG. 11 shows that treatment of bonnethead shark epigonal conditioned medium with protease reduces growth inhibitory activity against tumor cell lines. Protease treatment reduces growth inhibitory activity to less than half of growth inhibitory activity in conditioned medium compositions which have not been treated with protease. Treatment with proteinase K reduces growth inhibitory activity by approximately one-third. Treatment of bonnethead shark epigonal conditioned medium with trypsin does not reduce growth inhibitory activity against tumor cell lines.

Figure 12:
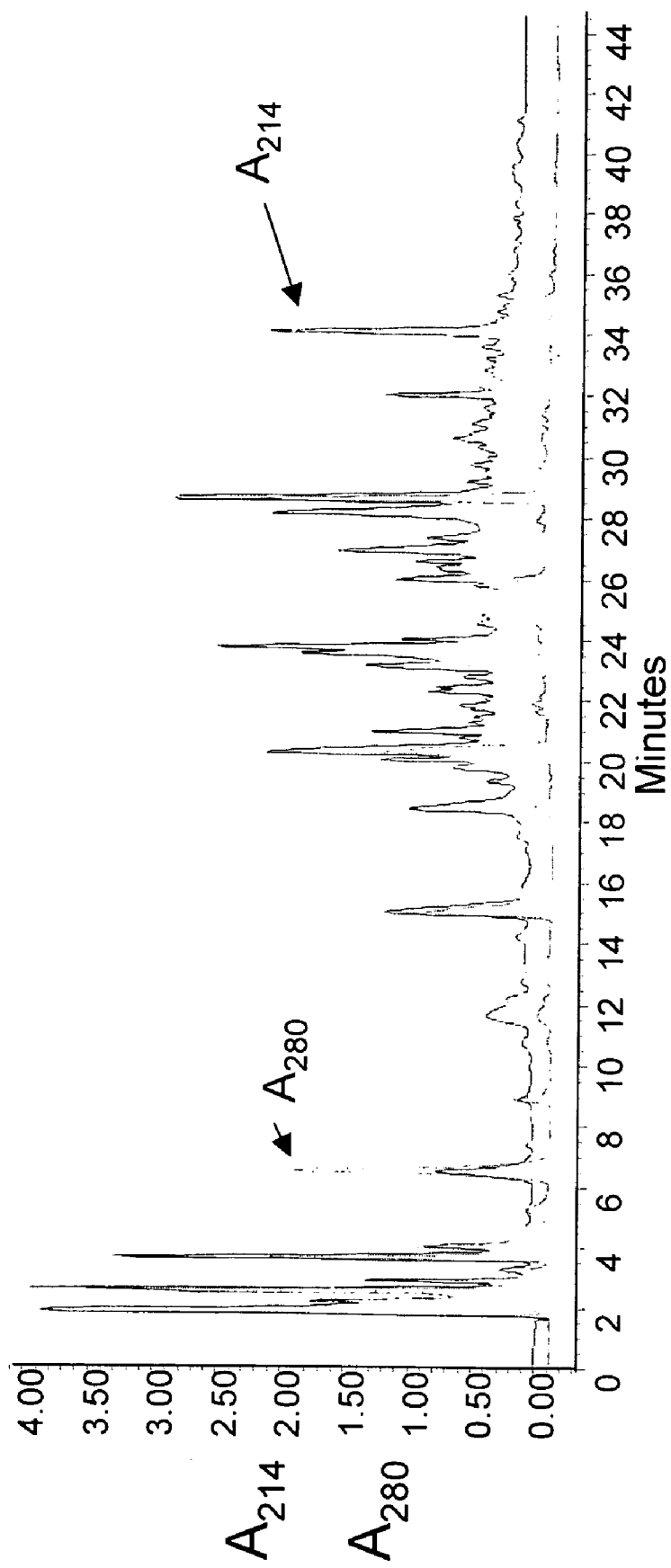
FIG. 12 shows tryptic fragments from bonnethead shark epigonal conditioned medium separated on reverse-phase C18 high-pressure liquid chromatography (HPLC) with 1% B/min water acetonitrile gradient at 1 ml/min flow rate. Absorbance at 214 nm (top, solid line) and absorbance at 280 nm (bottom, dashed line).
Figure 13:
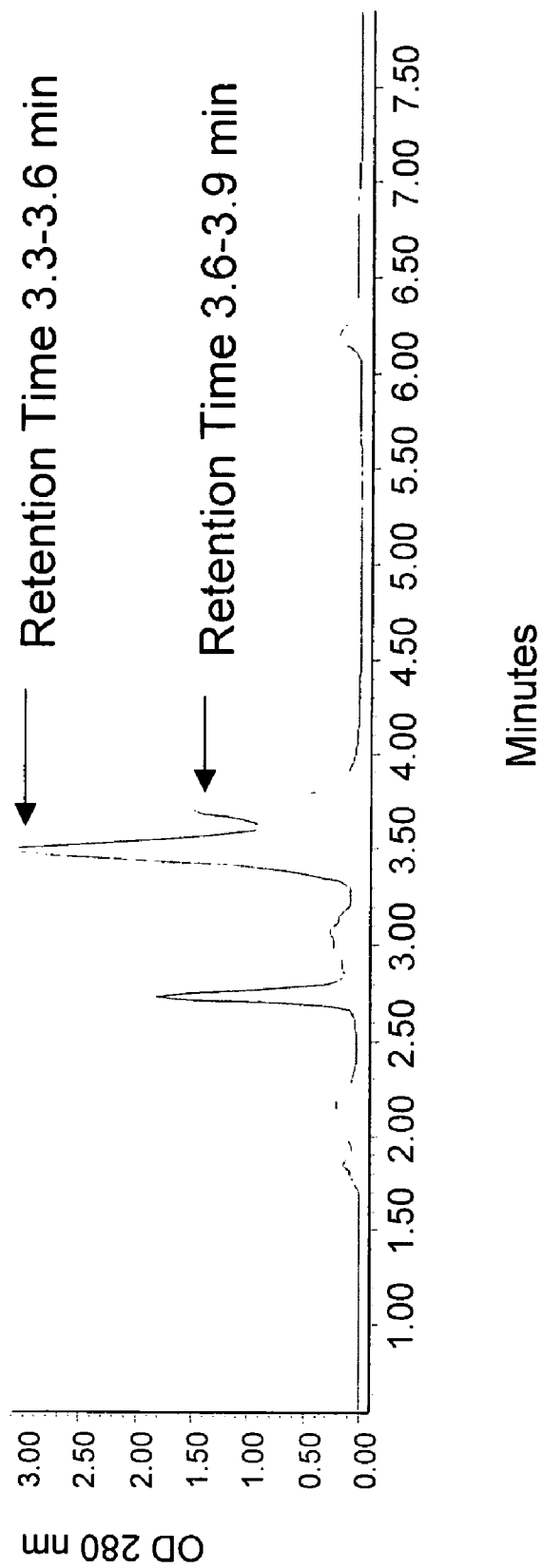
FIG. 13 shows high resolution of peak fractions eluting early from reverse-phase C18 HPLC. Active fractions elute between 3.3-3.6 min and 3.6-3.9 min.

FIG. 12 shows tryptic fragments from bonnethead shark epigonal conditioned medium on reverse-phase C18 HPLC with 1% B/min water acetonitrile gradient at 1 ml/min flow rate. Many peptide fragments are generated, and high resolution of peak fractions eluted early (retention times 3.3-3.6 and 3.6-3.9 min) is shown in FIG. 13. Fractions eluting with retention times 3.3-3.6 and 3.6-3.9 min demonstrate enhanced growth inhibitory activity at lower protein concentrations (see FIG. 10) compared with untreated bonnethead shark epigonal conditioned medium.

Figure 14:
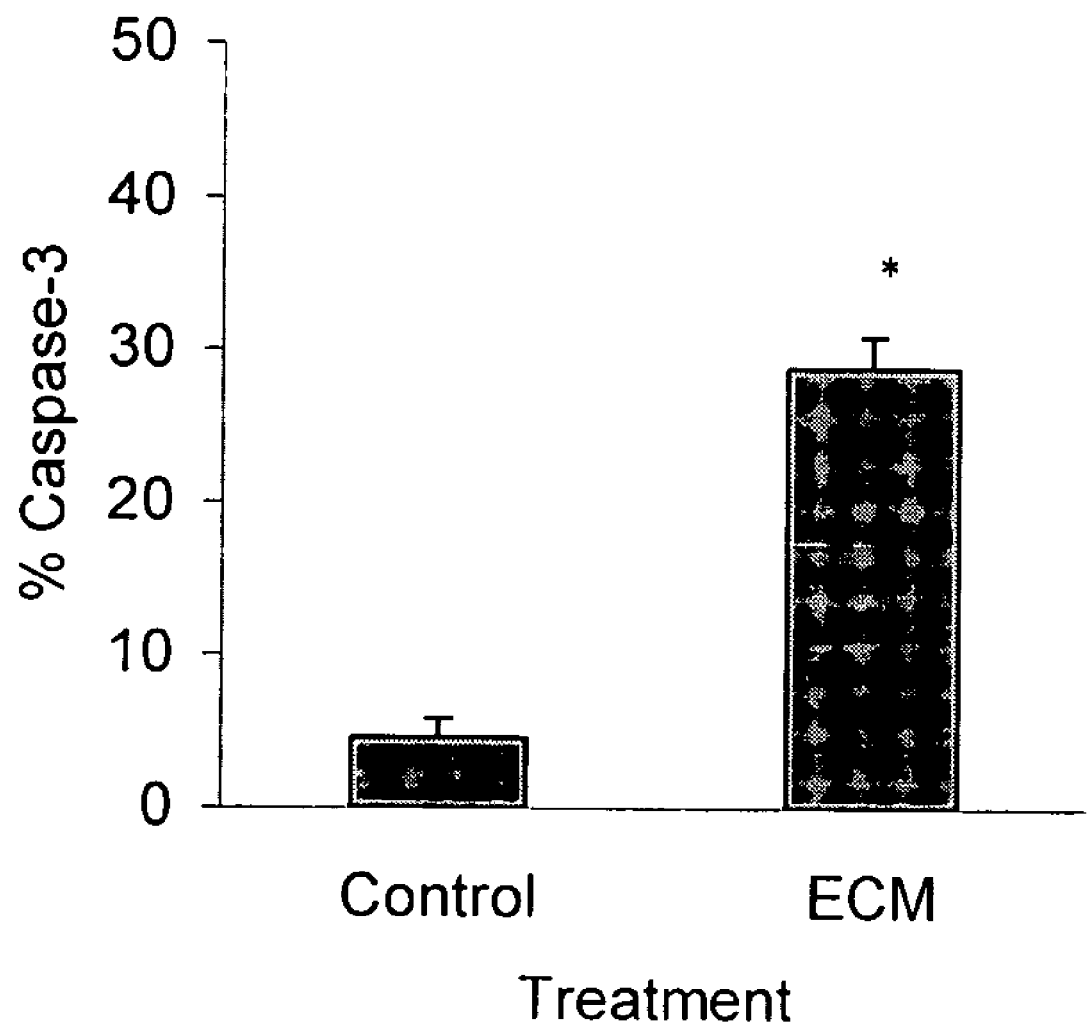
FIG. 14 shows induction of apoptosis in tumor cells (Daudi) by bonnethead shark epigonal conditioned medium (ECM), as measured by caspase-3.
Figure 15:
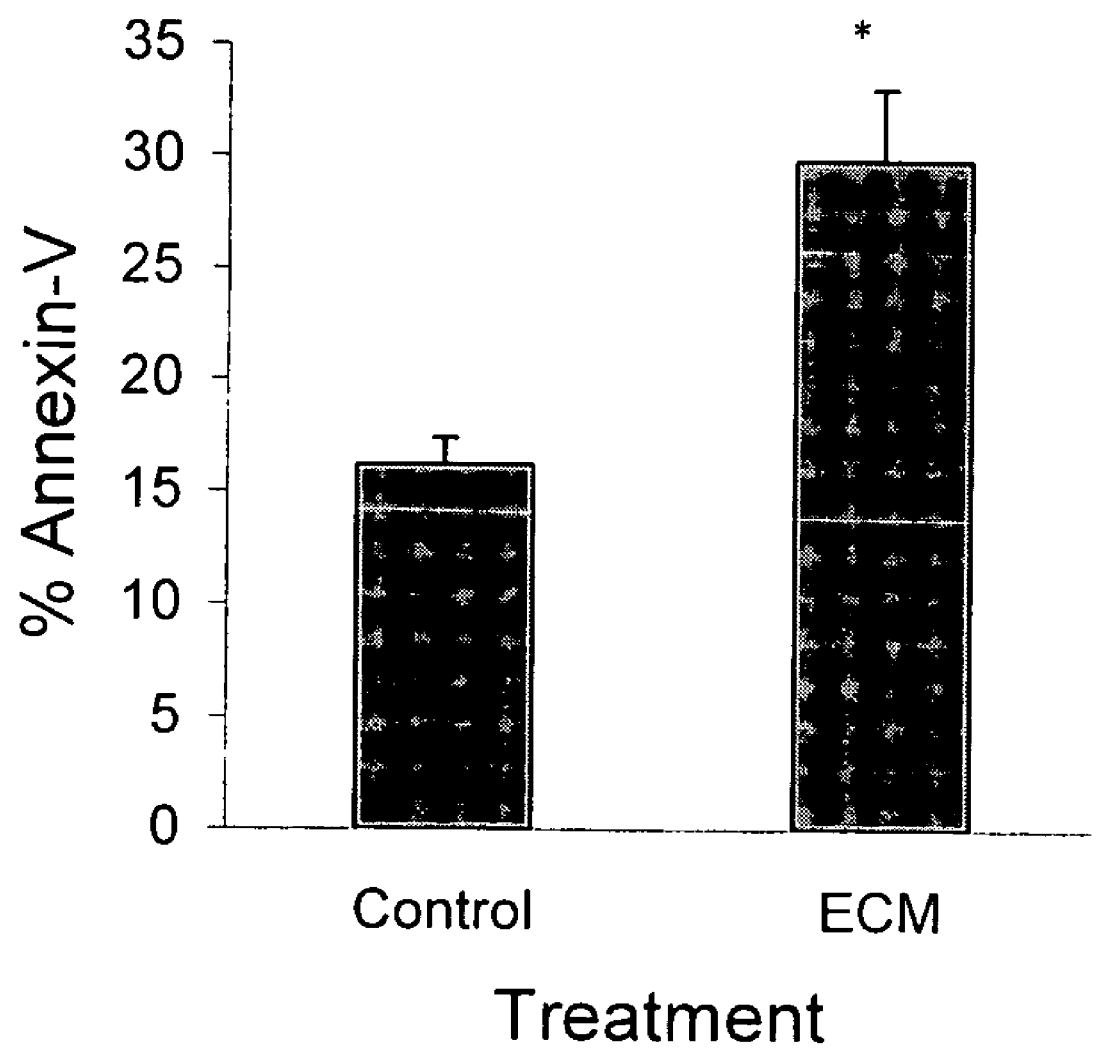
FIG. 15 shows induction of apoptosis in tumor cells (Daudi) by bonnethead shark epigonal conditioned medium (ECM), as measured by Annexin-V.

FIG. 14 shows induction of apoptosis in tumor cells (Daudi) by bonnethead shark epigonal conditioned medium, as measured by caspase-3. Caspase-3 is a key intermediate in apoptotic pathways. Bonnethead shark epigonal conditioned medium results in 30% occurrence of apoptosis in Daudi tumor cells compared with less than 5% apoptosis occurrence in untreated tumor cells. FIG. 15 shows induction of apoptosis in tumor cells (Daudi) by bonnethead shark epigonal conditioned medium, as measured by Annexin-V. Annexin-V is a marker that labels cell membranes of apoptotic cells. Treatment of Daudi cells with bonnethead shark epigonal conditioned medium increases occurrence of apoptosis in Daudi tumor cells by two-fold.

The molecules or molecular aggregates isolated from the conditioned media described herein comprise a protein or proteins having molecular weights or aggregate molecular weights ranging from 6000 Da to greater than 100 kDa. The proteins may comprise subunits having molecular weight less than 100 kDa. Ultrafiltration using a membrane having a molecular weight cutoff can be used to concentrate the liquid preparations described herein. Preferably the MWCO is 3 kDa-30 kDa, and more preferably the MWCO is about 10 kDa. The molecules or molecular aggregates isolated from conditioned media obtained from epigonal organs of lemon shark and bonnethead shark are partially heat labile at 56° C. and completely heat labile above 75° C.

The present invention includes therapeutic compositions comprising as an active ingredient an effective amount (e.g., final concentration between 0.1 µg/ml and 1 mg/ml)) of the conditioned media compositions described herein, and therapeutic methods comprising the use of the conditioned media compositions described herein. Therapeutic compositions and methods developed utilizing conditioned media compositions described herein include anti-tumor treatments (i.e., cancer). For example, irreversible anti-tumor activity has been demonstrated against human malignant melanoma and mouse fibrosarcoma.

EXAMPLES

Example 1

Bonnethead sharks (*Sphyrna tiburo*) are a common shark species found off the Gulf coast of Florida, USA. The sharks used in this Example were caught in nets and transported live to Mote Marine Laboratory. Sharks were maintained in flow-through tanks at Mote Marine Laboratory for short periods of time. Mature animals, both male and female, were used in this Example. Epigonal tissue was collected from healthy bonnethead sharks. The epigonal tissue was collected under aseptic conditions. The tissue was carefully rinsed with sterile elasmobranch-modified phosphate buffered saline (E-PBS) to remove any external blood or other body fluids. The tissue was used fresh, immediately following excision from the animal. The tissue was kept cold at 4° C. for 10-15 minutes until dissection was complete before culturing. The E-PBS used was 0.45 M NaCl, 0.01 M $NaH_2PO_4$ and was pH adjusted to 7.2-7.4 by titrating with 1 N HCl. The E-PBS was filter sterilized through 0.2 μm filter before use. Any gonadal tissue remaining with the epigonal tissue was removed by careful dissection using sterile dissection tools. The epigonal tissue was minced into small (2-5 $mm^2$) pieces with sterile scissors and forceps. The pieces were placed into 75 $mm^2$ sterile tissue culture flasks with elasmobranch-modified RPMI (E-RPMI; 20-40 mL, depending on size of tissue). A small volume was preferred since it was more convenient to manipulate. E-RPMI used in this example was 1.04 g of the cell culture medium RPMI without phenol red (available from Sigma as R8755) dissolved in 80 mL $dH_2O$. The osmolarity of the cell culture medium was adjusted to 970 mOsm by adding 2.16 g urea and 1.11 g NaCl, resulting in final concentrations of 360 mM urea and 188 mM NaCl. Antibiotics were added at final concentrations of 50 U penicillin G, 50 μg streptomycin sulfate, 0.1 mg neomycin/mL (available from Sigma as P3364). Amphotericin B was added at a final concentration of 0.25 μg/mL. Sodium bicarbonate was added and the pH was adjusted to 7.2-7.4. The volume was brought to 100 mL with $dH_2O$. E-RPMI was filter sterilized through a 0.2 μm filter before use. The cultures were incubated at 25° C. in 5% $CO_2$ for 2-4 days, with the length of time within this range not significantly altering the resultant activity. Conditioned media was harvested by removing cells with centrifugation at 20,000×g for 25 minutes at 4° C. This was repeated twice. To test this preparation against mammalian tumor cell lines, it was necessary to remove the salts and urea that comprise elasmobranch culture conditions. The conditioned media compositions were dialyzed against 50 mM ammonium bicarbonate at pH 7.4 at 4° C., and changed daily for 4 days. If it was not possible to dialyze immediately, the conditioned media compositions were frozen at −20° C. or −80° C. for unspecified lengths of time before dialysis with no loss in measurable biological activity. Dialysis was accomplished under cold conditions using dialysis tubing with 6000-8000 Da molecular weight cut-off and continual stirring. If precipitate was present in the tubing after dialysis was complete, the sample was briefly centrifuged at 20,000×g to remove precipitate. The dialyzed sample was frozen at −80° C. and then lyophilized until complete (typically 48 hours). Lyophilized samples were stored at −80° C. until use in assays. Protein concentration was determined by Bradford method on all samples before using in assays. After initial harvesting of conditioned media, once-cultured and incubated epigonal cells were placed into culture for a second incubation maintaining sterile conditions. Fresh E-RPMI was used for the second culture, and the cells were incubated for an additional 2 days. The second harvest of conditioned media had activity equivalent to the initial harvest. Lyophilized samples were resuspended in mammalian cell culture media before biological activity assays were conducted. Reconstituted samples were filtered through 0.2 μm sterile filters before use. Ultrafiltration using a membrane having a molecular weight cut-off value of about 30 kDa can be used to concentrate the liquid preparations described herein.

In vitro assays were conducted on the cancer cell lines A375.S2 (human malignant melanoma, American Type Culture Collection ATCC number CRL-1872), WEHI 164 (mouse fibrosarcoma, ATCC number CRL-1751), Daudi (human Burkitt's lymphoma, ATCC number CCL 213), MCF-7 (human breast carcinoma; ATCC number HTB-22), MDA-MB-435S (human breast ductal carcinoma; ATCC number HTB-129); and HCC38 (human breast ductal carcinoma; ATCC number CRL-2314), and on a normal cell line, HCC38BL (B lymphoblastoid cell line; ATCC number CRL-2346).

For A375.S2 cells, a cell culture medium having 0.97 g Minimum Essential Medium Eagle (available from Sigma as M0643) was dissolved in approximately 80 mL $dH_2O$. Antibiotics were added to a final concentration of 50 U penicillin G, 50 μg streptomycin sulfate, 0.1 mg neomycin/mL medium (available from Sigma as P3364). Amphotericin B was added at final concentrations of 0.25 μg/mL (Sigma A9528). Sodium bicarbonate was added and pH adjusted to 7.2-7.4. The medium was made to 90 mL with $dH_2O$, filter sterilized through 0.2 μm filter, and supplemented with 10% (by volume) fetal bovine serum (FBS) to make 100 mL final volume. Serum (available from Hyclone) was heat-inactivated at 56° C. for 30 minutes before use. Serum was aliquoted in sterile tubes and stored at −20° C. This solution was prepared fresh weekly and stored at 4° C.

For WEHI 164 cells, a cell culture medium having 1.04 g RPMI without phenol red was dissolved in approximately 80 mL $dH_2O$. Antibiotics were added at final concentrations of 50 U penicillin G, 50 μg streptomycin sulfate, 0.1 mg neomycin/mL medium (Sigma P3364). Amphotericin B was added to a final concentration of 0.25 μg/mL. Sodium bicarbonate was added and pH adjusted to 7.2-7.4. The volume of the medium was adjusted to 90 mL with $dH_2O$, filter sterilized with 0.2 μm filter, and 10% (by volume) heat inactivated FBS was added for a final volume of 100 mL. This solution was prepared fresh weekly and stored at 4° C.

For Daudi cells, a cell culture medium having 1.04 g RPMI without phenol red was dissolved in approximately 80 mL with $dH_2O$ for 100 mL of medium (final volume). These cells were cultured without antibiotics. Sodium bicarbonate was added and pH adjusted to 7.2-7.4. RPMI was filter sterilized through 0.2 μm filter before use. This solution was prepared fresh weekly and stored at 4° C. Heat-inactivated FBS (available from Hyclone) was added before use at 20% (by volume).

Once A375.S2 and WEHI 164 cells reached confluence, they were harvested by standard procedures and concentration-adjusted to $5 \times 10^4$ cells/mL and 100 μL cell suspension was added per well of 96 well microtiter plate. Cells were grown in the presence or absence of different concentrations of reconstituted lyophilized samples as prepared above. The lyophilizied conditioned media composition was thereby resuspended in culture medium and sterile filtered so that water soluble components were recovered and tested. All experiments were performed in at least triplicate. Cells were then grown in an incubator under a constantly humidified atmosphere containing 5% $CO_2$ at 37° C. for 3 days. Conditioned media was added in dilutions of 1:2, 1:4, 1:8, 1:16 and 1:32, corresponding to protein concentrations ranging from 4.5 mg/mL to 0.1 mg/mL final concentration. Cell growth inhibition was measured by the MTT (3-(4,5-dimethylthizaole-2-yl)-2,5-diphenyltetrazolium bromide) assay (available from Sigma as M2128) following 3 days of culture.

Daudi cells were distributed into 96 well microtiter plates. Cells were grown in the presence or absence of different concentrations of conditioned media prepared from the epigonal cells. Reconstituted lyophilized samples were prepared as described above. Conditioned media was added at concentrations of 0.125 to 1 mg/mL. The percentages of tumor cell growth inhibition presented in FIGS. 1 and 2 show that the conditioned media compositions described herein can inhibit in a dose-dependent manner the growth of the cells of the A375.S2 and WEHI 164 tumor cell lines. Doses of 2.2 and 4.5 mg/mL of the conditioned media inhibit growth at greater than 80% after three days of treatment, as shown in FIG. 1. A dosage of 1.1 mg/mL inhibits growth of WEHI 164 cells nearly 80%, whereas doses of 2.2 and 4.5 mg/mL inhibit growth of WEHI cells greater than 80%. In FIGS. 3 and 4, the effects of conditioned media on the Daudi cell cycle are shown. In Daudi cells, 250 µg/mL of the conditioned media potently inhibited DNA synthesis (S-phase) of Daudi cells by arresting cells in $G_0$ with little increase in apoptosis, as measured at 36 hours following exposure.

The average protein concentration of the conditioned media prepared in this Example was 9.16+/−0.63 mg/mL, with a sample size of 21. The protein content of the conditioned media was analyzed by Bradford method. SDS polyacrylamide gel electrophoresis (SDS-PAGE) was performed to characterize the molecular weights of the protein components. FIG. 5 shows that the conditioned media prepared from epigonal tissue from a bonnethead shark contains three major protein bands have molecular weights of approximately 43 kDa, 21 kDa, and 17 kDa.

Shark epigonal conditioned medium was tested against three breast carcinoma cell lines: MCF-7, MDA-MB-435S, and HCC38. Results are shown in FIGS. 8-10. MCF-7 cells were cultured in MEM containing 10% FBS and 0.01 mg bovine insulin/ml and were distributed in 96 well microtiter plates. Epigonal conditioned medium was added in final concentrations ranging from 0-2 mg/ml. Growth inhibition was measured using MTT as described, with maximal growth inhibition reaching 60% compared to control. Conditioned medium produced by bonnethead shark spleen cells in culture had minimal growth inhibitory activity (less than 10%). Bonnethead shark epigonal conditioned medium preferentially demonstrates growth inhibitory activity towards tumor cells, as demonstrated by lack of growth inhibitory activity towards a non-tumor cell (HCC38BL) line (see FIG. 9). Bonnethead shark epigonal conditioned medium inhibits growth of tumor cells by inducing apoptosis, or programmed cell death, in tumor cells (see FIGS. 14 and 15). Apoptosis was measured by using the key apoptotic intermediate, caspase-3, and by using the cell membrane indicator of apoptosis, Annexin-V. Tryptic peptide fragments were generated using in-liquid trypsin digestion followed by separation using reverse phase C18 HPLC and tested for bioactivity against human breast carcinoma cell line (MDA-MB-435S; see FIG. 10). Growth inhibitory activity was detected at 1 ug protein/ml, which represents at least 1000× increase in specific activity. Tryptic peptide fragments generated using in-liquid trypsin digestion followed by separation using reverse phase C18 HPLC are shown in FIGS. 12 and 13.

The conditioned media prepared in this Example demonstrated anti-proliferative activity on all tumor cell lines tested. The conditioned media prepared in this Example demonstrated preferential growth inhibitory activity against tumor cell lines compared with normal cells. The strongest inhibitions of greater than 80% were obtained with final concentrations of 1-4.5 mg/mL of the conditioned media on human malignant melanoma cells (A375.S2) and mouse fibrosarcoma cells (WEHI 164). For cells of human Burkitt's lymphoma, the strongest inhibition of growth cells was observed with a dosage of 250 µg/mL of the reconstituted lyophilized conditioned media. For breast cancer lines, the strongest inhibition was about 60% growth inhibition, observed at 1-2 mg protein/ml. Partially purified bonnethead shark epigonal conditioned medium prepared using trypsin digestion and separation on reverse-phase C18 HPLC resulted in a substantial (1000-fold) increase in growth inhibitory activity, with antitumor growth inhibitory activity demonstrated as low as 1 ug protein/ml.

Protease treatment partially destroys bonnethead shark epigonal conditioned medium growth inhibitory activity (see FIG. 11).

Example 2

Lemon sharks (*Negaprion brevirostris*) were caught off the Gulf Coast of Florida using hook and line. Epigonal tissue was obtained from fresh specimens and conditioned media were prepared as in Example 1. The conditioned media showed anti-proliferative activity on all tumor cell lines tested (A375.S2 and WEHI 164) and the effects of growth inhibition on dose are shown in FIGS. 6 and 7. Growth inhibition of WEHI 164 cells of >90% was achieved using a dose of approximately 3 mg/mL.

Example 3

Nurse sharks and clearnose skates were obtained from tanks maintained at Mote Marine Laboratory in Sarasota, Fla. Epigonal tissue was obtained from fresh specimens of nurse sharks and epigonal and Leydig organ tissues were obtained from fresh specimens from clearnose skates. Conditioned media were prepared as in Example 1. These preparations were evaluated for anti-tumor activity in various mammalian tumor cell lines. Inconsistent anti-tumor activity resulted from those preparations from nurse shark and clearnose skate immune tissue and they inhibited growth of less than 40% of A375.S2 cells and 50-70% of WEHI 164 cells.

It will be understood that the above-described compositions and methods are merely illustrative of applications of the principles of this invention and many other embodiments and modifications may be made without departing from the spirit and scope of the invention as defined in the claims.

What is claimed is:

1. A method for preparing a conditioned media composition comprising anti-tumor activity comprising the steps of:
   (1) providing tissue comprising epigonal organ or Leydig organ from an elasmobranch fish,
   (2) culturing and incubating the tissue in a cell culture medium under serum-free conditions, and
   (3) removing cells ftom the cell culture medium to produce a cell-free supernatant, wherein the cell culture medium has osmolarity of 800-1200 mOsm and comprises urea and a salt and tumor cell growth does not resume after removal of the conditioned media composition.

2. The method of claim 1 further comprising the steps of:
   (4) dialyzing the cell-free supernatant against water or a buffer solution to form a dialyzed supernatant, and
   (5) lyophilizing the dialyzed supernatant, and
   (6) reconstituting in a buffer.

3. The method of claim 1 further comprising the step of storing the cell-free supernatant at a temperature of 0°C or lower.

4. A conditioned media composition comprising anti-tumor activity, wherein the conditioned media composition is prepared by a method comprising:
   (1) providing tissue comprising epigonal organ or Leydig organ from an elasmobranch fish,
   (2) providing a cell culture medium having osmolarity of 800-1200 mOsm and comprising urea and a salt,
   (3) culturing and incubating the tissue in the cell culture medium under serum-free conditions, and
   (4) removing cells from the cell culture medium to produce a cell-free supernatant, wherein tumor cell growth does not resume after removal of the conditioned media composition.

5. The conditioned media composition of claim 4, wherein the cell-free supernatant is dialyzed, lyophilized and reconstituted in a buffer.

6. The conditioned media composition of claim 4, wherein the supernatant comprises one or more protein molecules.

7. The conditioned media composition of claim 6, wherein the one or more protein molecules comprises a subunit having molecular weight less than 100 kDa.

8. The conditioned media composition of claim 4, wherein molecules or molecular aggregates isolated from the supernatant are partially heat labile at or above 56° C.

9. A conditioned media composition comprising anti-tumor activity, wherein the conditioned media composition is prepared by a method comprising:
   (1) providing tissue comprising epigonal organ or Leydig organ from an elasmobranch fish,
   (2) providing a cell culture medium having osmolarity of 800-1200 mOsm and comprising urea and a salt,
   (3) culturing and incubating the tissue in the cell culture medium under serum-free conditions, and
   (4) removing cells from the cell culture medium to produce a cell-free supernatant,
   (5) removing protein extracts from the supernatant,
   (6) conducting trypsin digestion on the protein extracts to form tryptic peptides from the protein extracts, and
   (7) separating the tryptic peptides from the protein extracts, wherein tumor cell growth does not resume after removal of the conditioned media composition.

10. The conditioned media composition of claim 4, which preferentially targets malignant cells compared with non-malignant or normal cells, wherein growth inhibitory activity against malignant cells is approximately 40% to approximately 90% and growth inhibitory activity against non-malignant or normal cells is less than 12%.

11. The conditioned media composition of claim 4 which induces apoptosis in malignant tumor cells.

12. The conditioned media composition of claim 9, wherein the separation of tryptic peptides from the protein extracts comprises the use of high pressure liquid chromatography.

13. The conditioned media composition of claim 10, wherein the malignant tumor cells comprise human malignant melanoma, mouse fibrosarcoma, human Burkitt's lymphoma, or human breast cancer carcinoma.

14. The method of claim 1, wherein the anti-tumor activity comprises a 30% or greater increase in the percentage of tumor cells in the $G_0$ phase of the cell cycle.

15. The method of claim 1, wherein the anti-tumor activity comprises an 80% or greater decrease in the percentage of tumor cells in the S phase of the cell cycle.

16. The conditioned media composition of claim 4, wherein the tumor cell growth does not resume after washing and resuspension of cells that have been removed from the conditioned media composition in a fresh culture medium.

17. The conditioned media composition of claim 4, wherein the anti-tumor activity is not decreased by treatment with trypsin.

18. The conditioned media composition of claim 4, wherein the anti-tumor activity is diminished by approximately one-third by treatment with proteinase K, but is not reduced by treatment with trypsin.

19. The conditioned media composition of claim 9, wherein the tryptic peptides have approximately 1000 times greater tumor growth inhibitory activity over a conditioned media composition that has not been treated with trypsin digestion.

20. The conditioned media composition of claim 9, wherein the tryptic peptides exhibit tumor growth inhibitory activity at or above 1 μg/ml of tryptic peptides.

* * * * *